(12) United States Patent
Leitner et al.

(10) Patent No.: US 9,580,375 B2
(45) Date of Patent: *Feb. 28, 2017

(54) METHOD FOR PRODUCING FORMIC ACID BY $CO_2$ HYDROGENATION

(71) Applicant: RHEINISCHE-WESTFÄLISCHE TECHNISCHE HOCHSCHULE AACHEN, Aachen (DE)

(72) Inventors: Walter Leitner, Aachen (DE); Ulrich Hintermair, Rottendorf (DE); Sebastian Wesselbaum, Aachen (DE)

(73) Assignee: RHEINISCHE-WESTFÄLISCHE TECHNISCHE HOCHSCHULE AACHEN (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/677,432

(22) Filed: Apr. 2, 2015

(65) Prior Publication Data

US 2015/0210621 A1 Jul. 30, 2015

Related U.S. Application Data

(63) Continuation of application No. 13/978,994, filed as application No. PCT/EP2012/005011 on Jan. 4, 2012, now Pat. No. 9,073,842.

(30) Foreign Application Priority Data

Jan. 11, 2011 (DE) .................. 10 2011 000 077

(51) Int. Cl.
*C07C 51/00* (2006.01)
*C07C 51/083* (2006.01)
(Continued)

(52) U.S. Cl.
CPC .......... *C07C 51/00* (2013.01); *B01J 31/0237* (2013.01); *B01J 31/0284* (2013.01);
(Continued)

(58) Field of Classification Search
CPC ........... B01J 2231/625; B01J 2531/821; B01J 2531/922; B01J 2531/98; B01J 2540/32;
(Continued)

(56) References Cited

U.S. PATENT DOCUMENTS 4,855,496 A   8/1989  Anderson et al.
9,073,842 B2 * 7/2015  Leitner ............... C07C 51/083

FOREIGN PATENT DOCUMENTS

WO   2008116799 A1   10/2008
WO   2010149507 A2   12/2010

OTHER PUBLICATIONS

Zhao ("Electrochemical reduction of supercritical carbon dioxide in ionic liquid 1-n-butyl-3-methylimidazolium hexafluorophosphate" Journal of Supercritical Fluids 32 (2004), 287-291).*
(Continued)

*Primary Examiner* — Rosalynd Keys
*Assistant Examiner* — Amy C Bonaparte
(74) *Attorney, Agent, or Firm* — Schmeiser, Olsen & Watts, LLP

(57) ABSTRACT

The invention relates to a continuous method for producing formic acid from $CO_2$ and extracting the formic acid using compressed $CO_2$.

11 Claims, 5 Drawing Sheets

(51) Int. Cl.
*C07C 53/02* (2006.01)
*B01J 31/02* (2006.01)
*B01J 31/06* (2006.01)
*B01J 31/24* (2006.01)

(52) U.S. Cl.
CPC ....... *B01J 31/0285* (2013.01); *B01J 31/0288* (2013.01); *B01J 31/069* (2013.01); *B01J 31/2404* (2013.01); *C07C 51/083* (2013.01); *C07C 53/02* (2013.01); *B01J 2231/625* (2013.01); *B01J 2531/821* (2013.01); *B01J 2531/922* (2013.01); *B01J 2531/98* (2013.01); *B01J 2540/32* (2013.01)

(58) Field of Classification Search
CPC  B01J 31/0237; B01J 31/0284; B01J 31/0285; B01J 31/0288; B01J 31/069; B01J 31/2404; C07C 51/00; C07C 51/083
USPC .......................................... 518/715; 562/609
See application file for complete search history.

(56) References Cited

OTHER PUBLICATIONS

Wesselbaum "Continuous-Flow Hydrogenation of Carbon Dioxide to Pure Formic Acid using an Integrated scCO2 Process with Immobilized Catalyst and Base" Angewandte Chemie, Int. Ed, 2012, 51, p. 8585-8588, first published on Jul. 13, 2012.*

Jutz ("Ionic Liquids and Dense Carbon Dioxide: A Beneficial Biphasic System for Catalysis" Chem. Rev. 2011, 111, 322-353.*

Zhaofu Zhang et. al: "Hydrogenation of 1-10 carbon dioxide is promoted by a task-specific ionic liquid", Angew. Chem. Int. Ed., vol. 47. 2008. pp. 1127-1129.

Phillip G. Jessop et. al.: "Homogeneous catalytic hydrogenation of supercritical carbon dioxide", Nature, vol. 368. Feb. 7, 1994 (Feb. 7, 1994), pp. 231-233.

International Search Report; PCT/EP2012/050111; Int'l File Date: Jan. 4, 2012; Rheinische-Westfälische Technische Hochschule Aachen, 3 pgs.

Cole-Hamilton "Homogenous Catalysis—New Approaches to Catalyst Seperation, Recovery, and Recycling" Science, vol. 299, 2003, pp. 1702-1706.

\* cited by examiner

METHOD FOR PRODUCING FORMIC ACID BY $CO_2$ HYDROGENATION

CROSS REFERENCE TO RELATED APPLICATIONS

This application is a continuation application of U.S. patent application Ser. No. 13/978,994, filed Jul. 10, 2013 entitled METHOD FOR PRODUCING FORMIC ACID BY $CO_2$ HYDROGENATION, which is a 35 U.S.C. §371 National Stage application of PCT/EP2012/05011 filed Jan. 4, 2012, which claims the priority and benefit of German Patent Application No. 10 2011 000 077.1 filed Jan. 11, 2011.

FIELD OF TECHNOLOGY

The following relates to the field of formic acid production, in particular with high purity and in large scale, by means of $CO_2$ hydrogenation.

BACKGROUND

Formic acid is a versatile commercially used reagent of the chemical industry. It is essential for many chemical applications and could also be used in the future—assuming an efficient preparation—for storage of hydrogen and/or carbon monoxide within the energy and chemical industries. Formic acid is industrially obtained by means of the catalytic conversion of carbon monoxide with sodium hydroxide or methanol, and subsequent hydrolysis. This process is insofar disadvantageous, however, since the purification of aqueous formic acid is problematic because formic acid forms an azeotrope and has a tendency to dissociate again at high temperatures.

The preparation of formic acid by hydrogenation of $CO_2$ was proposed as an alternative. This reaction is indeed problematic because the $\Delta G$ for this reaction is positive, that is, a preparation is not thermodynamically possible purely from the educts. The hydrogenation of $CO_2$ is possible if a salt or adduct formation of the produced formic acid is carried out by adding stabilizers, generally bases. Several methods have been proposed to accomplish this purpose, such as, for example, in Zhang et al, *Angewante Chemie*, 47, 2008, p. 1127-1129, in which an excess of ionic fluid is utilized.

All of the methods according to the prior art currently require the use of (over)stoichiometric amounts of stabilizer in the form of a base. Only formic acid salts or base adducts are formed thereby. These must be cleaved in a separate method step in order to release pure formic acid. They present thus substantially the same problems during the separation of formic acid from the used base as the above methods, in which formic acid is prepared from carbon monoxide. The used catalyst must additionally be separated in most methods according to the prior art due to toxicological and economical reasons as well as for the stability of the product. These separation and processing steps make the previous methods unattractive from the energetic and economical point of view.

Thus, there is a need to find a method for producing formic acid by means of $CO_2$ hydrogenation, which is able to overcome for the most part the disadvantages described above and by means of which an efficient, continuous reaction control is possible.

SUMMARY

A method for hydrogenation of $CO_2$ for production of formic acid is accordingly proposed, which comprises the steps of:
a) Catalytic reaction of $CO_2$ with hydrogen in the presence of a base for production of formic acid
b) At least partial discharge of the produced formic acid from the reaction area of step (a) using compressed $CO_2$
c) Release of the formic acid while removing $CO_2$ from step (b)

Now surprisingly, it turns out that the disadvantages existing in most applications can be overcome by means of this kind of reaction control, such that its use on a commercial scale is possible.

It has been discovered that at least one or several of the following advantages can be achieved by means of such a method in most applications within the invention:

A material and energy intensive separation of the formic acid from the stabilizers (needed for the hydrogenation) is omitted because the formic acid escapes from the reaction area when compressed $CO_2$ is used. The activity of the catalyst is furthermore retained.

The deposited formic acid is so pure that it can be directly used for most technical processes without a purification step The steps for separation of the formic acid from the salt/base adduct compounds that were necessary until now are omitted The method can be carried out continuously, which facilitates or even makes possible an efficient commercial use.

The term "compressed $CO_2$" in the sense of the invention means herein in particular that $CO_2$ is used in gaseous (but compressed), super-critical or liquid form. $CO_2$ concentrations within the range between $\geq 0.2$ g/ml and $\leq 1.2$ g/ml, preferably between $\geq 0.3$ g/ml and $\leq 0.9$ g/ml are preferred. The $CO_2$ can also be (only) liquid and/or super-critical, depending on the concrete configuration of the method.

The term "using compressed $CO_2$" (step b) should not be understood as so limiting that exclusively compressed $CO_2$ is used in step (b) (even though this is a preferred embodiment of the invention). Depending on the concrete embodiment of the method, liquid mixtures of compressed $CO_2$ with other solvents, among which are preferred alcohols and detergents, can also be taken into consideration.

The term "discharging" in the sense of the invention means or implies in particular that the formic acid is dissolved in $CO_2$ and can thus be extractively removed via the steam pressure or by means of a combination of these effects from the reaction area. The term "discharging" is however to be understood in the broadest sense and is not limited thereto.

The method is preferably continuously carried out.

The term "continuously" in the sense of the invention means or implies in particular that the catalyst is exposed to a flow of compressed $CO_2$ (which contains $H_2$ and if required cosolvents), which at the same time serves as transport vector for the discharged formic acid. The isolation of formic acid after the reactor is preferably likewise continuously carried out by lowering the $CO_2$ concentration (decompressing and/or heating) or by washing out of the $CO_2$ flow.

According to a preferred embodiment of the invention, the $CO_2$ is compressed during the reaction in step (a). This facilitates the implementation of the method, since the work can in this way be carried out predominantly within the same pressure range. The $CO_2$ is available predominantly (that is up to ≥80%), but still even more preferably exclusively (that is, up to ≥99%) in liquid or in super-critical state during the reaction in step (a).

The $CO_2$ removed in step (c) is accordingly fed back in step (a) pursuant to a preferred embodiment.

According to a preferred embodiment of the invention, the base in step (a) includes an ionic liquid and/or an ionic compound.

The term "ionic liquid" is understood to mean especially compounds that are available as a salt or a salt mixture having the formula $[A]_n^+ [Y]^{n-}$ with n=1 or 2 having a melting point under reaction conditions which is lower than the reaction temperature.

This has proven to be advantageous for the method according to the invention, since in this way one or several of the following advantages can be achieved with most applications:

- The base is not extracted and there is no solvent loss or cross contamination as a result of the low steam pressure in step (b)
- The balance of the hydrogenation reaction can be positively shifted in direction toward product formation by means of suitable ionic liquids
- The continuous extraction of the formed formic acid makes possible the catalytic use of stabilizers (alkaline ionic liquid), wherewith further purification steps can be eliminated
- Many metal catalysts, in particular transition metal catalysts, display an excellent efficiency and stability in ionic liquids as solvents
- Considerable amounts of $CO_2$ can be dissolved in ionic liquids (up to 70 mol % depending on the compound and concrete application) without the need for an excessive volume expansion of the ionic liquid itself and thus influence the physical properties thereof (low viscosity, high solubility of other gases, such as hydrogen, increased material transport, etc.)

According to a preferred embodiment of the invention, the ionic liquid is preferably selected from the group of onium ion compounds, preferably containing imidazolines, quart. Ammonium salts, quart. Phosphonium salts, alkylated pyridinium salts or mixtures thereof.

Additionally preferred herein is one or several of the following compounds:
- 4-methylbutylpyridinium bis(trifluoromethylsulfonyl)imides ([MBP][$NTf_2$]) and 1-ethyl-3-methyl-imidazolium bis(trifluoromethylsulfonyl)imides ([EMIM][$NTf_2$]) or their analogs with other suitable anions
- 1-(N,N-dethylaminoethyl)-2,3-dimethylimidazolium bis(trifluoromethylsulfonyl)imide ([EAMMIM][BA]) or analogs with other suitable anions*
- 1-(N,N-dimethylaminoethyl)-2,3-dimethylimidazolium salts
- 1,3-di(N,N-dimethylaminoethyl)-2-methylimidazolium salts
- as well as 1-alkyl-3-methylimidazolium ions, pyrrolidinium, pyridinium, tetraalkylammonium or tetraalkylphosphonium ions (organic cations) in combination with tetrafluoroborate, hexafluorophosphate, halogenide anions, bis(trifluoromethanesulfonyl)amide, trifluoromethanesulfonate, dicyanimide, tosylate, carboxylate ($R-COO^-$ with R=H, alkyl, aryl, etc., for example, R=H formiate, R=$CH_3$) acetate or n-alkylsulfates.

[T.N. "dethylaminoethyl" is clearly misspelled in the source. It likely means "diethylaminoethyl" or possibly also "dimethylaminoethyl."]

According to another preferred embodiment of the invention, the base comprises a high molecular-weight amine in step (a). These are understood to be amines (preferably polyamines) with a molecular weight of 1000 Da and higher. It has also been found that these amines have a solubility that is so low in compressed $CO_2$ that they are likewise especially suitable for the method according to the invention. Amine or diamine dendrimers are preferred. Examples of these compounds are polymer-bound (for example, polystyrene) amines, polyamines based on, for example, benzylamine and ethylenediamine or other monomers, et cetera, or dendrimers, arboroles and cascade molecules containing amine functions (for example, $N((CH_2)_nN((CH_2)_nN((CH_2)_nN((CH_2)_nN( ... ))))_3$ with n≥2).

According to another preferred embodiment of the invention, the base is at least in part, preferably predominantly (that is, up to ≥80% by weight), even more preferably exclusively (that is, up to ≥99% by weight) bonded or immobilized on a fixed carrier. This has proven to be particularly advantageous, since in this way the discharge of the produced formic acid can take place particularly easily.

The term "bond" should be understood herein in the broadest sense and should comprise covalent bonds as well as also physical bonds (in the sense of "inclusions", et cetera) or bonds via electrostatic, hydrogen bridge or ion-like bonds.

Porous carriers or carriers such as silicates, aluminates, zeolites, activated carbon, graphites, MOFs, graphite foams (carbon aerogels) and/or carbon nanotubes are preferred.

According to a preferred embodiment of the invention, the hydrogenation in step (a) takes place in the presence of a transition metal catalyst. This has been shown to be particularly effective. Catalysts containing one or several of the following transition metals: Ru, Co, Rh, Ir, Fe, Ni, Pd and Pt are particularly preferred. Heterogeneous catalysts, nanoparticule catalysts or homogeneously charged catalysts are again particularly preferred. The particularly preferred catalysts contain one or several of the following compounds:

[Ru(Cl)$_2$(COD)]$_n$ or [Ru(cod)(methallyl)$_2$] with PBu$_4$TPPMS (as precursor materials/catalyst precursor)

Polystyrene-$(CH_2)_3$NH(CSCH$_3$)-{RuCl$_3$(PPh$_3$)}
"Si"—$(CH_2)_3$NH(CSCH$_3$)-{RuCl$_3$(PPh$_3$)}
[RhCl(PPh$_3$)$_3$], [{RhCl(cod)}$_2$], [RhCl(TPPTS)$_3$], [(dcp-b)Rh(acac)], [RuCl$_2$\{P(CH$_3$)$_3$\}$_4$], [RUH$_2$ \{P(CH$_3$)$_3$\}$_4$] and [RuCl$_2$(OAc)(PMe$_3$)$_4$] (catalyst precursor)

[Cp*Ir(phen)Cl]Cl and [Ir$^{III}$PNP] (catalyst precursor)

According to a preferred embodiment of the invention, the catalyst has a solubility of ≤0.1 g/l in compressed $CO_2$ in step (a).

According to a preferred embodiment of the invention, at least step (a) is carried out with a $CO_2$ pressure of ≥10 bar, preferably ≥20 bar and most preferably ≥40 bar to ≤500 bar.

According to a preferred embodiment of the invention, step (a) is carried out with a $H_2$ pressure of ≥5 bar, preferably ≥10 bar and most preferably ≥20 bar to ≤60 bar.

Preferably at least one part—preferably the predominant part, that is, ≥80%, even more preferably substantially all, that is ≥99%—of the $CO_2$ extracted in step (c), is fed back in step (a) and/or (b).

The invention likewise refers to a device for carrying out the method according to the invention.

The aforementioned as well as the claimed components to be utilized according to the invention described in the exemplary embodiments are not subject to any exceptions with regard to their size, shape, material selection and technical concept, so that the selection criteria known within the application field can be applied without restrictions.

BRIEF DESCRIPTION

Further details, features and advantages of the object of the invention are obtained from the dependent claims as well as the following description of the corresponding drawings, in which several exemplary embodiments of the method according to the invention are presented as examples. The drawings show:

DETAILED DESCRIPTION

Example I

The invention will be analyzed on the basis of Example I, which is to be understood purely as an example.

Figure 1:
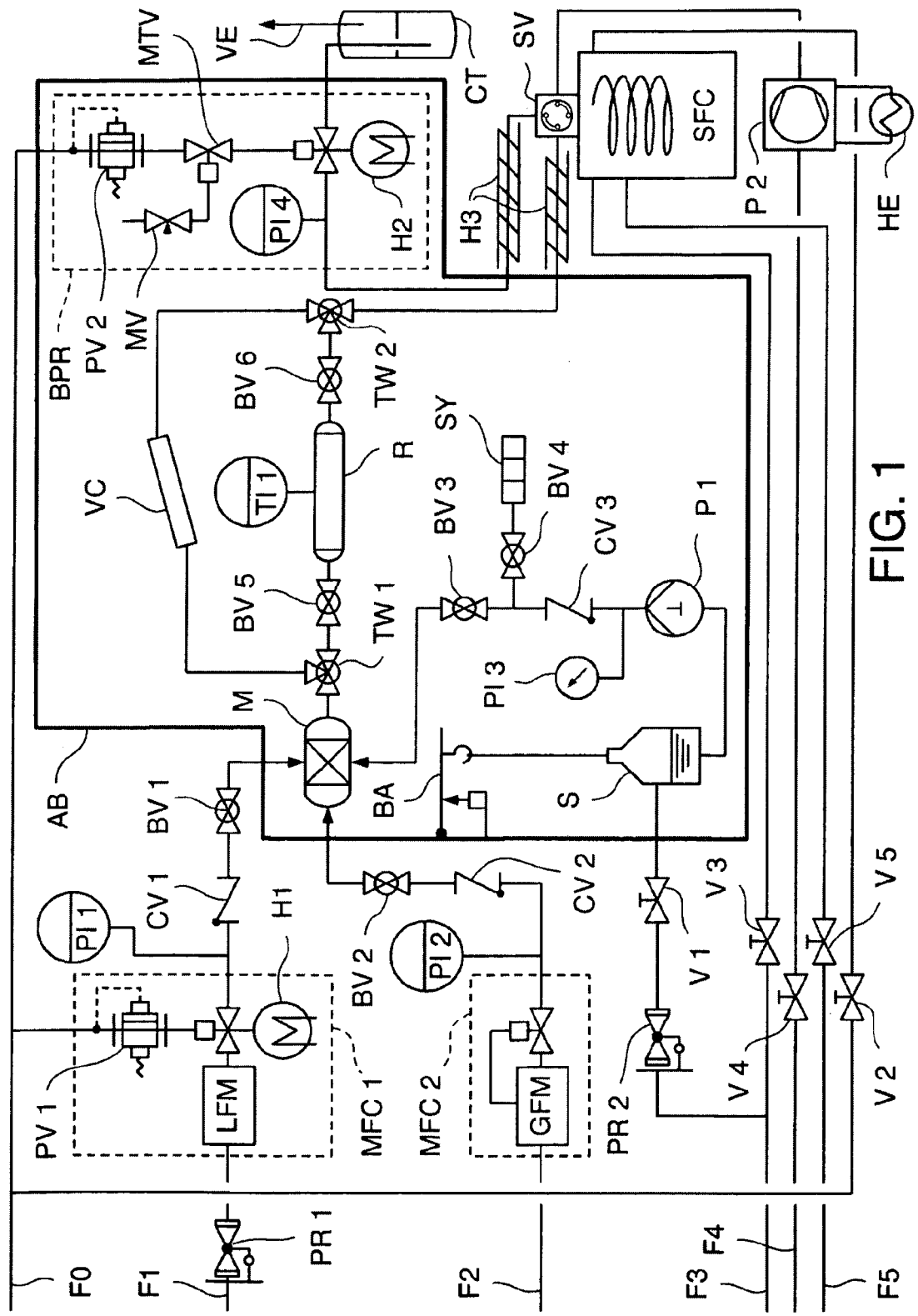
FIG. 1 shows a flow diagram of an arrangement for carrying out the method pursuant to the invention according to a first embodiment of the invention (Example I)

FIG. 1 shows a flow diagram of an arrangement for carrying out the method pursuant to the invention according to a first embodiment of the invention (Example I), wherein:
F0=compressed air (6 bar), F1=liquid $CO_2$, F2=$H_2$, F3=$N_2$, F4=liquid $CO_2$ (approx. 40-70 bar), F5=$H_2$, PR=reduction valve, MFC=mass flow controller, LFM=flowmeter, GFM=gas flowmeter, H=heat, PI=pressure indicator, PV=proportional valve, CV=check valve, BV=ball valve, AB=incubator, V=lockable valve, M=mix chamber, S=reservoir for cosolvents or derivatization reagent, BA=scale, P=piston pump, SY=flushing syringe, TW=three-way valve, R=reactor, VC=high pressure visual cell, TI=temperature indicator, BPR=back pressure regulator valve, MTV=magnetic tunneling valve, MV=metering valve, CT=cold trap, VE=ventilation, SV=high pressure switchover valve, HE=heat exchanger, SFC=supercritical fluid chromatograph.

The method according to the invention is (essentially) carried out in the incubator AB. The $CO_2$ is first mixed with the $CO_2$ in the mixing chamber M (a solvent can also be supplied via suitable lines, such as, for example, F0, if required). The hydrogenation subsequently takes place in the reactor R, and the produced formic acid then exits (for the most part) the reaction area together with the nonreacted $CO_2$. A chromatograph "SFC"—which can also be omitted in commercial applications or other exemplary embodiments—is provided in order to control the reaction. Then if required, a separation of $CO_2$ takes place in the pressure stabilizer BPR by decompression of the compressed mobile phase, which can be discharged via the proportional valve PV2 and can again be fed back at PV1 for further hydrogenation. Then in the cold trap CT together with the ventilation VE, the separation of the (pure) formic acid from the $CO_2$ takes place. The separated $CO_2$ can here again be fed back, depending on the application.

Physical Description of Progress of the Experiment

1. Production of the Immobilized Catalyst

Aminated silica gel SiliaBond® Diethylamine (SiliCyle Inc., particle size 40-63 nm, average pore size 600 nm, surface area 500 m²/g, pore volume 0.8 ml/g) was dried for 3 hours at 80° C. and at 0.1 mbar and stored under argon atmosphere. A parent solutions [sic] were [sic] applied under argon atmosphere for the exact dosage of the metal complex. For this purpose, 40 µmol of $[Ru(Cl_2)(COD)]_n$ were weighed and dissolved in exactly 5 ml of DCM (c=8 µmol/ml). From this was removed 0.34 ml (2.701 µmol) which was added to a 3 equivalent $PBu_4TPPMS$. The mixture was evaporated in a high vacuum until dry and was then dissolved in $[EMIM][NTf_2]$ ($c_{Ru}$=0.0027 mol/l). The precursor dissolved in $[EMIM][NTf_2]$ was now blended with silica gel SiliaBond® Diethylamine mixed with DCM and dried in a high vacuum, so that the charge of the carrier amounted to 44.2% by weight. A two-hour drying process at 0.1 mbar and 50° C. took place after this. The supported catalyst/stabilizer system was obtained as a powder.

2. Implementation of the Hydrogenation

A hydrogenation was carried out within a test setup utilizing the solid carrier of I pursuant to the flow diagram of FIG. 1. The procedure was carried out as follows:

Filling of the Reactor

The filling of the tube reactor was carried out under an argon atmosphere. The reaction tube was opened at one end for this purpose and closed with 1 cm of glass wool. The desired amount of supported catalyst/stabilizer system (m=4.257 g, V=9.36 cm³, $n_{catalyst}$=2.701 µmol) was then added and held in place with 1 cm glass wool and the reaction tube was closed and installed in the apparatus.

Startup and Operation of the Apparatus

The ball valves in the reactor remained initially closed and the bypass was opened in order to start the apparatus. The $CO_2$ volume flow was set to 150 $ml_N$/min and the BPR was set to 200 mbar. Once the desired pressure was reached, it was switched over to the reactor in order to preset herein a pressure of 200 bar. Once the pressure was reached, it was switched over again to the bypass and the $H_2$ volume flow was dosed. Once this system pressure was reached, then the $CO_2$ volume flow was set to 100 $ml_N$/min and the $H_2$ volume flow was set to 10 $ml_N$/min. Once the values remained constant, the flow was switched from the bypass to the reactor. This was the time point at which the reaction was started. The reaction temperature amounted to 50° C. The reaction was ended after 137 hours of operation.

Sampling

In order to sample the product, which was continuously extracted with the aid of the $CO_2$, the extraction flow was fed toward the BPR via a steel capillary in a cold trap filled with purified water and glass beads. The cold trap was periodically replaced and the content was analyzed as to formic acid.

Figure 2:
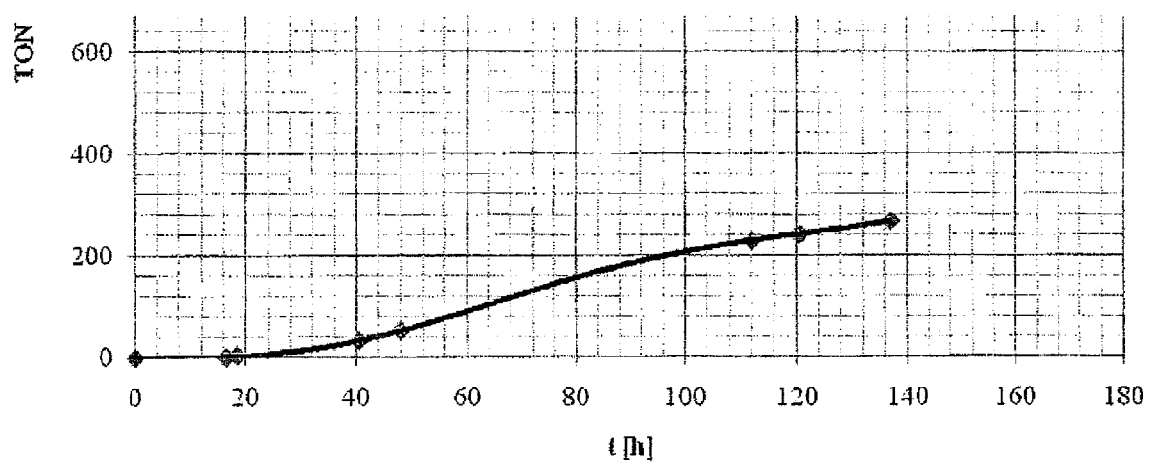
FIG. 2 shows a diagram which illustrates the "TON" (Turnover Number), the verifiable amount of formic acid in the $CO_2$ flow relative to the metal content of the catalyst (mol/mol) during the implementation of the method on the basis of Example I.

FIG. 2 shows the progression of the turnover number plotted against time. Turnover numbers (TON) with a maximum TON=214 with 137 hours of continuous operation were achieved (with still fully non-optimized conditions).

Example II

The same reaction apparatus as in Example I and shown in FIG. 1 is used in the example described herein, wherein a continuously stirred tank reactor is utilized instead of a flow tube. The catalyst provided herein is homogeneously dissolved in an ionic liquid phase.

1. Production of the Catalyst Solution

For the exact dosage of the metal complex 24 μmol of [Ru(cod)(methallyl)$_2$] and 84 μmol of PBu$_4$TPPMS (ratio 1:3.5) were dissolved under argon atmosphere in 3 ml of DCM, and of this amount 0.25 ml (2 μmol of [Ru]) were transferred into another Schlenk flask. In addition, 2 equivalents of EMIMCl were added by means of a parent solution in DCM. Then was added 1 ml of the ionic liquid 1-(N,N-dethylaminoethyl)-[sic] 2,3-dimethylimidazolium bis(trifluoromethylsulfonyl)imide ([EAMMIM][BTA]) and the mixture was stirred for 2 h at 70° C. in a high vacuum to remove the DCM.

2. Implementation of the Hydrogenation

A hydrogenation within a test setup was carried out according to the flow diagram of FIG. 1 using the catalyst/stabilizer solution produced in step 1. The procedure was carried out therein as follows:

Filling of the Reactor

The catalyst/stabilizer solution was transferred under an argon atmosphere into a 10 ml stirred tank reactor and its ball valves were closed. The reactor prepared in this way was installed in the apparatus.

Startup and Operation of the Apparatus

The startup and operation of the apparatus took place as described in Example I with the following difference: A constant CO$_2$ volume flow of 200 ml$_N$/min and a H$_2$ volume flow of 20 ml$_N$/min at 200 bar were set in the bypass operation. The flow was switched over from bypass to reactor and the reactor was thus flushed for 30 minutes in order to equalize the atmosphere in the reactor with that during the continuous operation. The flow was then again switched over to bypass for 20 h in order to allow a balanced concentration of formic acid in the reactor, which improves the extraction from the beginning. The CO$_2$ and H$_2$ flow was again fed through the reactor after 20 h. This time point will be considered below as the starting point of the continuous reaction. The reaction was stopped after 211 hours of operation.

Sampling

The sampling was carried out as described in Example I.

Figure 3:
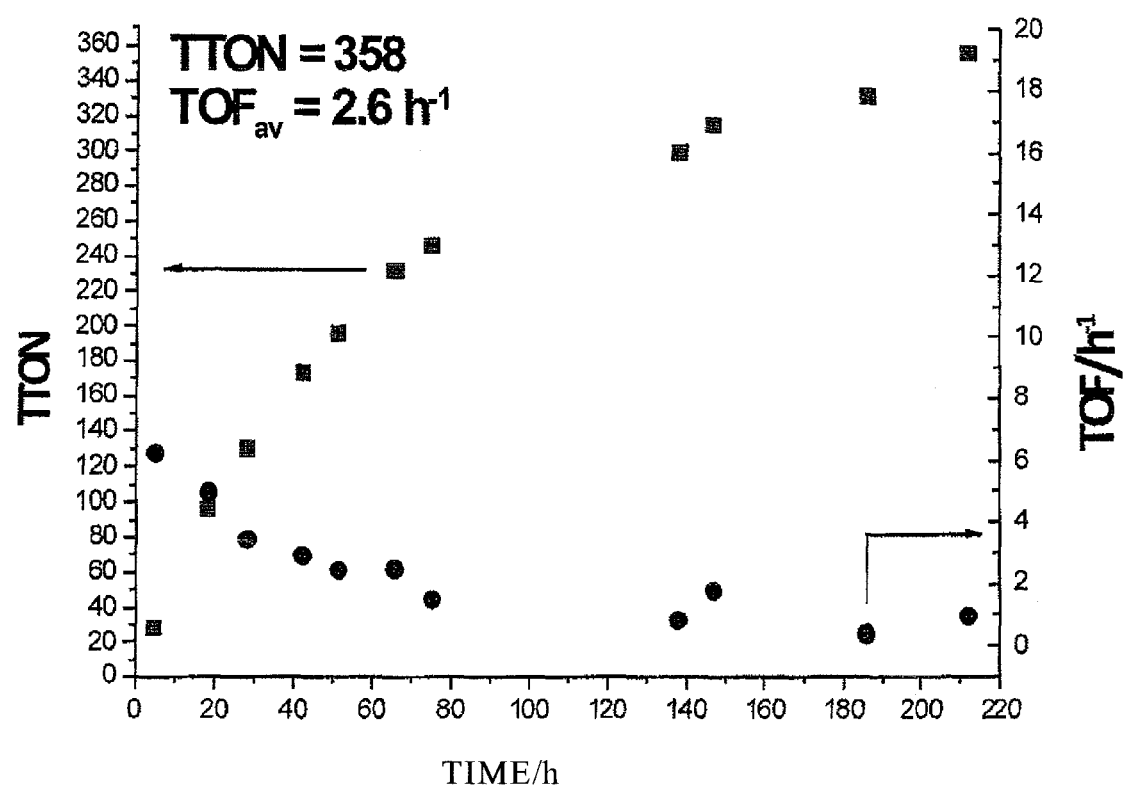
FIG. 3 shows a diagram which illustrates the progression of the total turnover number (TTON) and the turnover frequency (TOF) plotted against time during the implementation of the method on the basis of Example II.
Figure 4:
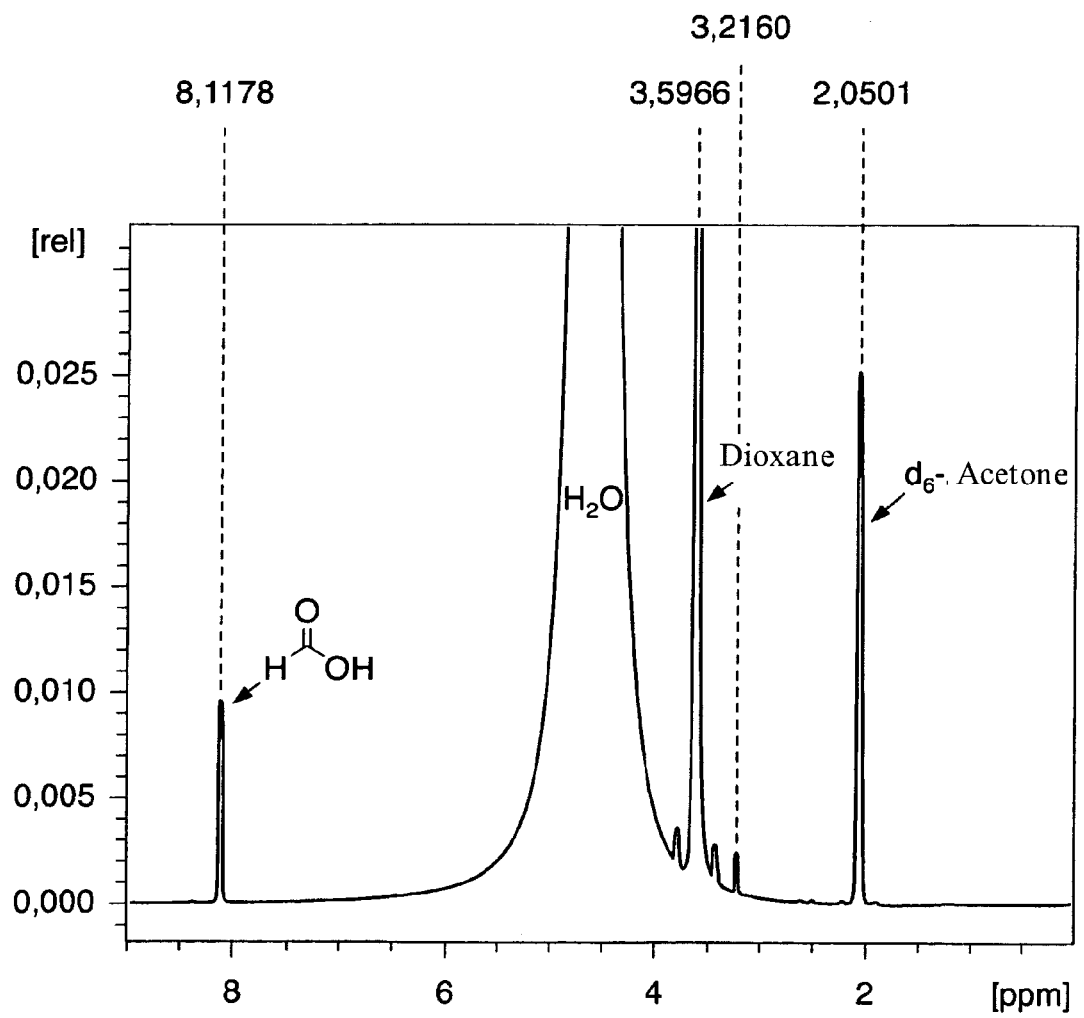
FIG. 4 shows an NMR spectrum of a sample during the method on the basis of Example II.

FIG. 3 shows the progression of the total turnover number (TTON) and the turnover frequency (TOF) plotted against time. A TTON of 358 could be reached therein after 211 hours of continuous operation. FIG. 4 shows as an example the $^1$H-NMR analysis of the cold trap content with dioxane as internal standard. With the signal at 3.2 ppm there are traces of methanol, with which the apparatus was previously cleaned.

Example III

The example described herein, like Example II, uses only a heterogeneous polymer-bound amine QuadraPure™-DMA instead of an amino functionalized ionic liquid.

1. Production of the Catalyst Solution

For the exact dosage of the metal complex an amount of 24 μmol of [Ru(cod)(methallyl)$_2$] and 84 μmol of PBu$_4$TPPMS (ratio 1:3.5) was dissolved in 3 ml of DCM under an argon atmosphere and 0.25 ml (2 μmol of [Ru]) were transferred into another Schlenk flask. As additive were added 2 equivalents of EMIMCl, likewise by means of a parent solution in DCM. Then 1 ml of the ionic liquid ([EAMMIM][BTA]) was added and the mixture was stirred for 2 h at 70° C. in a high vacuum to remove the DCM.

2. Implementation of the Hydrogenation

A hydrogenation was carried out within a test setup according to the flow diagram of FIG. 1 using the catalyst/stabilizer solution produced in 1. The procedure was carried out as follows:

Filling of the Reactor

Into the 10 ml stirred tank reactor was added 0.5 g of QuadraPure™-DMA as well as the catalyst/stabilizer solution under an argon atmosphere and its ball valves were closed. The reactor prepared in this way was installed in the apparatus.

Startup and Operation of the Apparatus

The startup and operation of the apparatus took place as described in Example II with the following difference: A constant CO$_2$ volume flow of 200 ml$_N$/min and a H$_2$ volume flow of 20 ml$_N$/min at 200 bar were set in the bypass operation. The flow was switched over from bypass to reactor in order to start the continuous operation. The reaction was stopped after 190 hours of operation.

Sampling

The sampling was carried out as described in Example I.

Figure 5:
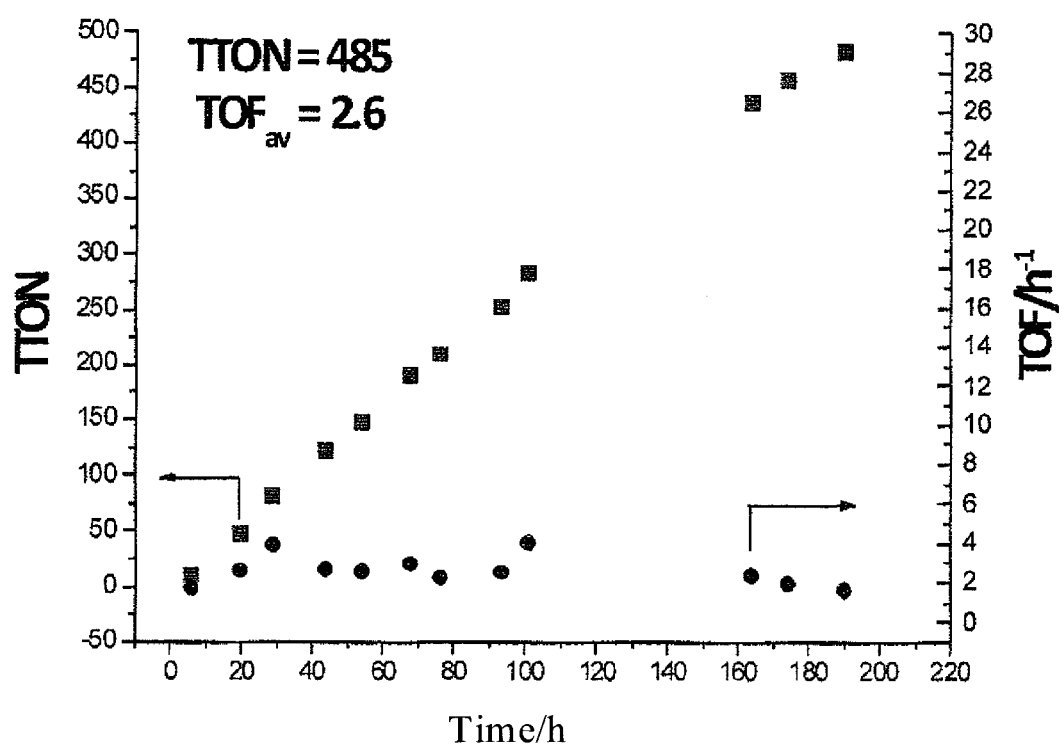
FIG. 5 also shows a diagram which illustrates the progression of the total turnover number (TTON) and the turnover frequency (TOF) plotted against time during the implementation of the method on the basis of Example III.

FIG. 5 shows the progression of the total turnover number (TTON) and the turnover frequency (TOF) plotted against time. A TTON of 485 could be reached therein after 190 hours of continuous operation.

The individual combinations of the components and the features of the already-mentioned embodiments are exemplary; the replacement and substitution of these teachings with other teachings contained in this publication and with those of the cited publications are likewise expressly contemplated. The person skilled in the art realizes that variations, modifications and other embodiments than those described herein can likewise be implemented without deviating from the spirit and scope of the invention. The above-mentioned description is accordingly exemplary and is not to be seen as a limitation. The wording used in the claims does not exclude further components or steps. The indefinite article "a" does not exclude the meaning of a plural. The mere fact that specific measurements are recited in different claims does not signify that a combination of these measurements cannot be advantageously used. The scope of the invention is defined in the following claims and the corresponding equivalents thereof.

The invention claimed is:

1. A method of continuously hydrogenating CO$_2$ to formic acid, comprising the following steps:
    a) producing formic acid by a catalytic reaction of CO$_2$ with hydrogen in the presence of a base, in a reaction area;
    b) at least partially discharging the produced formic acid using compressed CO$_2$, which is compressed during the reaction in step a), from the reaction area of step (a); and
    c) releasing the formic acid while removing the CO$_2$ from step (b);
    wherein the base is an amine bonded to a fixed carrier.

2. The method of claim 1, wherein the CO$_2$ is available in a compressed state during the reaction in step (a).

3. The method of claim 1, wherein the base in step (a) comprises an ionic liquid.

4. The method of claim 3, wherein the ionic liquid is imidazolines, quaternary ammonium salts, quaternary phosphonium salts or mixtures thereof.

5. The method of claim 1, wherein the base in step (a) is a high molecular-weight amine.

6. The method of claim 1, wherein the hydrogenation in step (a) takes place in the presence of a transition metal catalyst.

7. The method of claim 1, wherein at least step (a) is carried out with a $CO_2$ pressure of $\geq 10$ bar.

8. The method of claim 1, wherein at least a part of the $CO_2$ extracted in step (c) is fed back in step (a) or (b).

9. A method for hydrogenation of $CO_2$ to formic acid, comprising the following steps:
   a) producing formic acid by a catalytic reaction of $CO_2$ with hydrogen in the presence of a base bonded to a fixed carrier, in a reaction area, wherein the base is an amine;
   b) at least partially discharging the produced formic acid using compressed $CO_2$, which is compressed during the reaction in step a), from the reaction area of step (a); and
   c) releasing the formic acid while removing the $CO_2$ from step (b).

10. The method of claim 9, wherein the $CO_2$ is available in compressed state during the reaction in step (a).

11. The method of claim 9, wherein at least a part of the $CO_2$ extracted in step (c) is fed back to step (a) and/or (b).

* * * * *